United States Patent [19]
Hossack et al.

[11] Patent Number: 5,740,128
[45] Date of Patent: *Apr. 14, 1998

[54] ULTRASONIC HARMONIC IMAGING SYSTEM AND METHOD

[75] Inventors: John A. Hossack, Palo Alto; Christopher R. Cole, Cupertino; Jian-Hua Mo, Milpitas, all of Calif.

[73] Assignee: Acuson Corporation, Mountain View, Calif.

[*] Notice: The term of this patent shall not extend beyond the expiration date of Pat. No. 5,608,690.

[21] Appl. No.: 642,528

[22] Filed: May 3, 1996

Related U.S. Application Data

[63] Continuation-in-part of Ser. No. 397,833, Mar. 2, 1995, Pat. No. 5,608,690.

[51] Int. Cl.$^6$ .................................................. H04B 1/02
[52] U.S. Cl. ................................. 367/138; 367/7; 367/11
[58] Field of Search ................................. 367/7, 11, 138, 367/103, 105; 128/661.01, 660.08, 660.09, 662.02; 73/618, 619, 621, 624, 625, 626, 633, 641

[56] References Cited

U.S. PATENT DOCUMENTS

| | | |
|---|---|---|
| 3,953,825 | 4/1976 | Kino et al. . |
| 4,016,750 | 4/1977 | Green . |
| 4,140,022 | 2/1979 | Maslak . |
| 4,395,912 | 8/1983 | Hassler . |
| 4,403,311 | 9/1983 | Tournois . |
| 4,403,314 | 9/1983 | Tournois . |
| 4,446,740 | 5/1984 | Wilson et al. . |
| 4,456,982 | 6/1984 | Tournois . |
| 4,458,342 | 7/1984 | Tournois . |
| 4,550,607 | 11/1985 | Maslak et al. . |
| 4,699,009 | 10/1987 | Maslak et al. . |
| 4,870,971 | 10/1989 | Russell et al. . |
| 4,974,558 | 12/1990 | Katakura et al. . |
| 5,014,712 | 5/1991 | O'Donnell . |
| 5,105,814 | 4/1992 | Drukarey et al. . |
| 5,113,706 | 5/1992 | Pittaro . |
| 5,142,649 | 8/1992 | O'Donnell . |
| 5,218,869 | 6/1993 | Pummer . |
| 5,228,007 | 7/1993 | Murakami et al. . |
| 5,235,982 | 8/1993 | O'Donnell . |
| 5,301,674 | 4/1994 | Erikson et al. . |
| 5,322,068 | 6/1994 | Thiele et al. . |
| 5,608,690 | 3/1997 | Hosack et al. ............... 367/138 |

OTHER PUBLICATIONS

Transmit Aperture Processing for Nonlinear Contrast Agent Imaging, *Ultrasonic Imaging* 18, 77–105 (1996), Article No. 0005, pp. 77–105, 1996.

Peter N. Burns, PH.D., "Harmonic imaging adds to ultrasound capabilities", Echo Enhancement, pp. AU7–AU10.

P. N. Burns, et al., "Harmonic Power Mode Doppler Using Microbubble Contrast Agents", 1994 Ultrasonics Symposium, pp. 1547–1550 (1994).

P.H. Chang, et al., "Second Harmonic Imaging and Harmonic Doppler Measurements with Albunex®", 1994 Ultrasonics Symposium, pp. 1551–1554 (1994).

V. Uhlendorf, et al., "Nonlinear Acoustical Response of Coated Microbubbles in Diagnostic Ultrasound", 1994 Ultrasonics Symposium, pp. 1559–1562 (1994).

C.B. Buckhardt et al.; "Ultrasound Axicon: a device for focusing over a large depth", Ultrasound Axicon, vol. 54, No. 6, 1973, pp. 1628–1630.

(List continued on next page.)

*Primary Examiner*—Daniel T. Pihulic
*Attorney, Agent, or Firm*—Brinks Hofer Gilson & Lione

[57] ABSTRACT

A method for imaging a target including a nonlinear contrast agent includes the steps of transmitting ultrasonic energy at a fundamental frequency and receiving reflected ultrasonic energy at a harmonic of the fundamental frequency. The ultrasonic energy is transmitted in power bursts, each having a respective envelope shape, wherein the envelope shapes rise gradually to a respective maximum value and fall gradually from the respective maximum value. Ultrasonic energy in the transmit beam is focused in an elongated high power region, as for example by means of a line focus.

54 Claims, 4 Drawing Sheets

OTHER PUBLICATIONS

Pi Hsien Chang, et al., "Second Harmonic Imaging and Harmonic Doppler Measurements with Albunex®", IEEE Transactions on Ultrasoncis, Ferroelectrics, and Frequency Control., vol. 42, No. 6, Nov. 1995, pp. 1020–1027.

Synchronous Dynamic Focusing for Ultrasound Imaging; G. Manes, et al.; IEEE Transactions on Ultrasonics, Ferroelectrics, and Frequency Control, vol. 35, No. 1, Jan. 1988; pp. 14–21.

Properties of Swept FM Waveforms in Medical Ultrasound Imaging; C.R. Cole; 1991 Ultrasonics Symposium, pp. 1243–1248.

Frequency Synthesis by Phase Lock; William F. Egan, Ph.D., Senior Engineering Specialist GTE Products Corporation; Lecturer in Electrical Engineering University Santa Clara, Robert E. Krieger Publishing Company, Malabar, Florida 1990; pp. 14–29.

Stanford Research Systems; Synthesized Function Generator; Model DS345–30 MHz Function & Arbitrary Waveform Generator; 1994; pp. 8–13.

Stanford Research Systems; Scientific and Engineering Instruments 1994–1995; pp. 171–176.

IEEE Transactions on Ultrasonics, Ferroelectrics, and Frequency Control, vol. 37, No. 5, Sep. 1990, Ultrasonic Nondiffracting Transducer for Medical Imaging, Jian–Yu Lue et al., pp. 438–447.

IEEE Transactions on Ultrasonics, Ferroelectrics, and Frequency Control, vol. 39, No. 3, May 1992, "Experimental Verification of Nondiffracting X Waves", Jian–yu Lu et al., pp. 441–446.

IEEE Transactions on Ultrasonics, Ferroelectrics, and Frequency Control, vol. 39, No. 1, Jan. 1992, "Non–diffracting X Waves–Exact Solutions to Free–Space Scalar Wave Equation and Their Finite Aperture Realizations", Jian–yu Lu et al., pp. 19–31.

"Synthesis of the driving functions of an array for propagating localized wave energy", J.E. Hernandez et al, J. Acoust. Soc. Am. 92 (1), Jul. 1992, pp. 550–562.

"Simulated Capillary Blood Flow Measurement Using a Nonlinear Ultrasonic Contrast Agent", B. Schrope et al., Ultrasonic Imaging 14, pp. 134–158 (1992).

P. Tournois; "Acoustical Imaging Via Coherent Reception of Spatially Coloured Transmissions"; 1980 Ultrasonics Symposium; pp. 747–750.

1

ULTRASONIC HARMONIC IMAGING SYSTEM AND METHOD

CROSS REFERENCE TO RELATED APPLICATION

This application is a continuation-in-part of U.S. patent application Ser. No. 08/397,833, filed Mar. 2, 1995 now U.S. Pat. No. 5,608,690. This application is hereby incorporated by reference in its entirety.

BACKGROUND OF THE INVENTION

This invention relates to ultrasound imaging systems, and in particular to improved methods for imaging nonlinear contrast agents with such systems.

Nonlinear contrast agents are described for example by V. Uhlendorf, et al., in "Nonlinear Acoustical Response of Coated Microbubbles in Diagnostic Ultrasound" (1995 Ultrasonic Symposium, pp. 1559–1562). Such agents possess a fundamental resonant frequency. When they are insonified with high intensity ultrasonic energy at this fundamental frequency, they radiate ultrasonic frequency at a harmonic of the fundamental frequency. Such contrast agents are often used to highlight regions containing blood loaded with the contrast agent. For example, in the case of a blood-filled chamber of the heart, the borders of the chamber can be distinguished more easily when contrast agent is used. Since the contrast agent generates harmonic ultrasound energy, echoes from tissue (containing no contrast agent) at the fundamental frequency may be eliminated by filtering at the receive beamformer.

Typically, such agents are used with an imaging system having a transmit beamformer that transmits ultrasonic energy at the fundamental frequency and a receive beamformer responsive to the harmonic. In order to image the contrast agent clearly, it is known to reduce energy at the harmonic in the transmit beam, and to reduce sensitivity of the receive beamformer to energy at the fundamental.

In the past, this has been done by using a burst of square or sine waves to form the transmit beam, and by using appropriate band pass or high pass filters in the receive beamformer. Though a large pulse count reduces energy at the harmonic, it reduces time resolution of the pulse, and therefore spatial resolution of the resulting image.

The present invention is directed to further improvements that enhance the imaging of such nonlinear contrast agents.

SUMMARY OF THE INVENTION

This invention relates to improvements to a method for imaging a target comprising a nonlinear contrast agent, which method comprises the steps of (a) transmitting ultrasonic energy at a fundamental frequency and (b) receiving reflected ultrasonic energy at a harmonic of the fundamental frequency.

According to a first aspect of this invention, the transmitting step includes the step of transmitting ultrasonic energy in power bursts, each power burst comprising a respective envelope shape, the envelope shapes rising gradually to a respective maximum value and falling gradually from the respective maximum value. This arrangement can reduce harmonic energy in the power burst.

According to a second aspect of this invention, the transmitting step includes the step of generating a transmit waveform and filtering the transmit waveform with a filter adapted to reduce ultrasonic energy in the transmit waveform at the harmonic of the fundamental frequency to at least −30 dB with respect to the fundamental frequency.

According to a third aspect of this invention, the transmitting step includes the step of generating a transmit waveform with a programmable waveform generator such that ultrasonic power in the transmit waveform at the harmonic of the fundamental frequency is reduced by at least −30 dB with respect to ultrasonic power in the transmit waveform at the fundamental frequency.

According to a fourth aspect of this invention, the transmitting step includes the step of focusing ultrasonic energy in a transmit beam having a line focus.

According to a fifth aspect of this invention, the transmitting step includes the step of focusing ultrasonic energy in a transmit beam having an elongated high power region by focusing at least first selected frequency components from at least a first plurality of transducer elements at a first range and focusing at least second frequency components from at least a second plurality of transducer elements at a second range.

DETAILED DESCRIPTION OF THE PRESENTLY PREFERRED EMBODIMENTS

Figure 1:
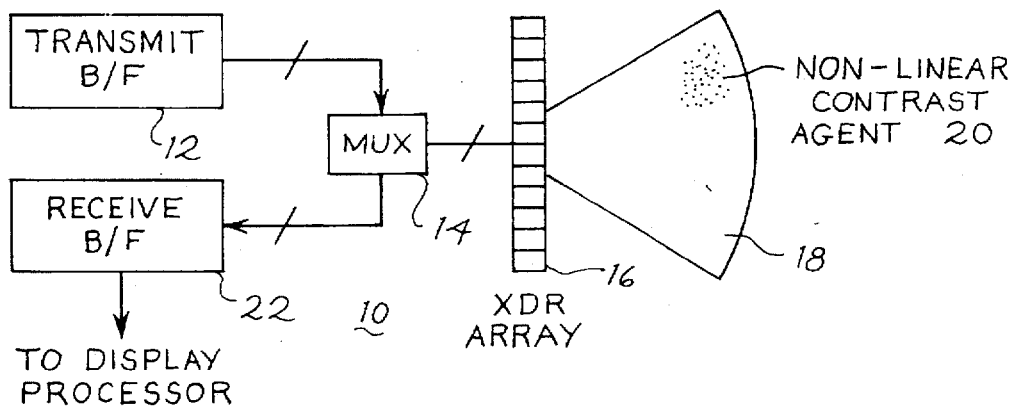
FIG. 1 is a block diagram of an ultrasonic imaging system suitable for use with the method of this invention.

The preferred embodiments described below are designed to reduce harmonic energy in the transmitted beam, and to provide an improved spatial distribution of fundamental energy in the transmitted beam. FIG. 1 shows generally an ultrasonic imaging system 10 which can be used to practice the method of this invention.

The system 10 includes a transmit beamformer 12 that supplies high voltage transmit waveforms via a multiplexer 14 to a transducer array 16. The transducer array 16, which can be any suitable type, generates an ultrasonic transmit beam in response to the transmit waveforms, and this transmit beam propagates outwardly through the subject 18 being imaged. In this case, the subject being imaged includes a nonlinear contrast agent 20, such as that described above. Any suitable contrast agent may be used, as long as it absorbs ultrasonic energy at a first frequency and radiates ultrasonic energy at a second frequency, different from the first frequency. In this example, the first frequency is referred to as the fundamental frequency, and the second frequency is a harmonic of the first frequency. As used herein, "harmonic" is intended broadly to include subharmonics and fractional harmonic energy (e.g. ½ or ³⁄₂ of the fundamental), as well as higher harmonics (e.g. 2 or 3 times the fundamental).

Ultrasonic energy radiated by the nonlinear contrast agent 20 at the harmonic frequency is received by the transducer array 16, focused by the receive beamformer 22, and displayed as an image by a display processor (not shown). As described above, the receive beamformer 22 includes conventional filters to substantially prevent reflected ultrasonic energy at the fundamental frequency from being imaged.

Figure 2:
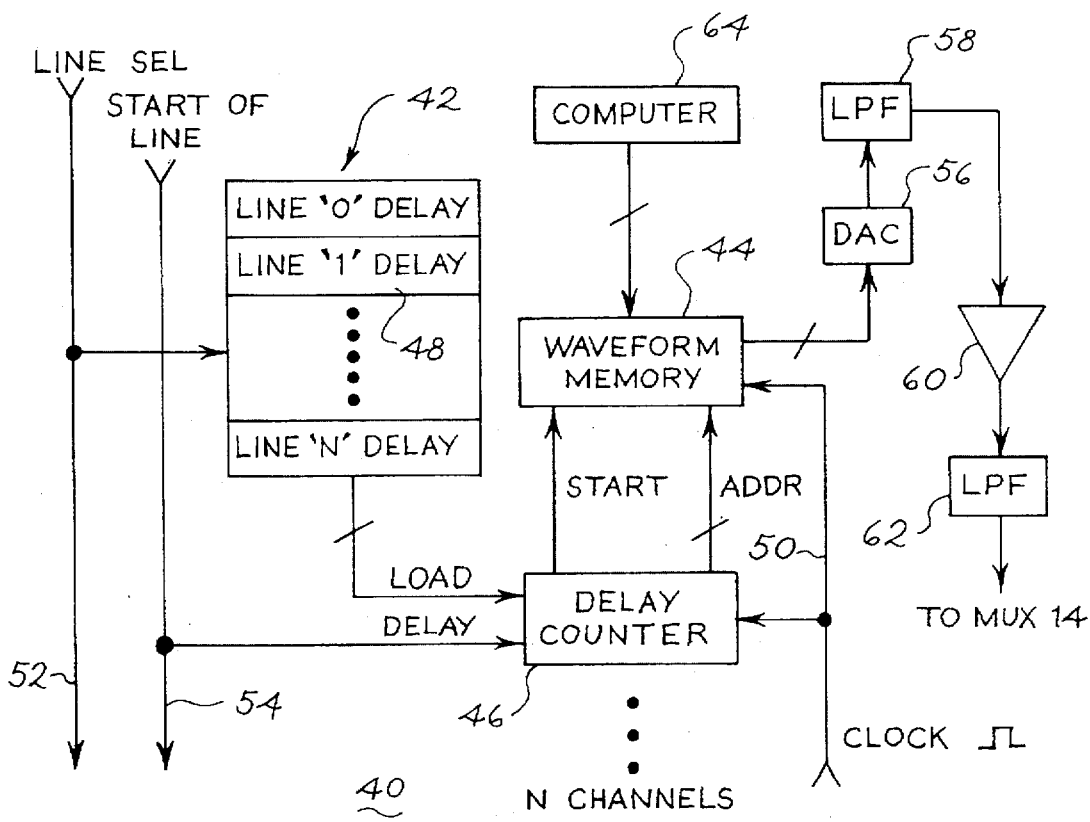
FIG. 2 is a block diagram of a transmit beamformer suitable for use in the system of FIG. 1.

Turning now to FIG. 2, this figure shows a block diagram of a first preferred embodiment 40 of the transmit beamformer of FIG. 1. As shown in FIG. 2, the transmit beamformer 40 includes N channels, one for each of the transducers of the transducer array 16 (FIG. 1). Each channel includes a delay memory 42, a waveform memory 44, and a delay counter 46 (FIG. 2).

The delay memory 42 includes 256 words 48, one for each possible steering angle or ultrasound transmit scan line. Each word 48 of the delay memory 42 is set equal to a negative number equal to the number of clock cycles on the clock signal line 50 that elapse between a start of line signal on line 54 and the first non-zero value of the associated waveform. For simplicity, it is assumed that zero is defined as a word 48 having the most significant bit equal to one all other bits equal to zero. Hence, the most significant bit becomes an enable signal for the waveform memory 44.

The waveform memory 44 in this embodiment stores a single waveform in digital form, which is used for all transmit scan lines. The waveform memory 44 can include for example 64 or 128 successive 8 bit words. The magnitude of each 8 bit word corresponds to the voltage amplitude at the respective position in the waveform. When the waveform memory 44 is read with a 40 MHz clock on the line 50, the resulting sequence of digital values defines a waveform approximately 1.6 to 3.2 microseconds in duration.

The delay memory 42 is not required, but it reduces memory requirements for the waveform memory 44. This is because the delay memory 42 eliminates the need to store a large number of leading zeros when the ultrasound line is steered at a large angle.

In use, each channel responds to a scan line selection signal on line 52 by loading the word 48 for the selected scan line into the delay counter 46. The delay counter 46 responds to a start of scan line signal on line 54 by incrementing the stored value with each cycle of the 40 MHz clock on line 50. When the counter 46 increments to zero, it enables the waveform memory 44. Subsequently generated values of the counter 46 (incrementing now from zero upwards) become address values for the waveform memory 44. As each word of the waveform memory 44 is addressed, the corresponding 8 bit word is read and applied to a digital to analog converter 56.

The analog output signal of the converter 56 is passed through a low pass filter such as a Bessel filter 58 to reduce sampling effects and then to an amplifier 60. The output of the amplifier 60 can be passed through an additional low pass filter 62 to improve harmonic rejection. The output of the low pass filter 62 is the transmit waveform discussed above that is applied to the respective transducer via the multiplexer 14 (FIG. 1). The low pass filters 58, 62 preferably provide a sharp cut-off with a low stop band level in order substantially to eliminate ultrasonic energy in the transmitted pulse at the harmonic frequency.

The transmit beamformer 40 utilizes values for the waveforms stored in the waveform memory 44 and the delays stored in the delay memory 42 that enhance insonification of the nonlinear contrast agent in the subject.

Figure 3:
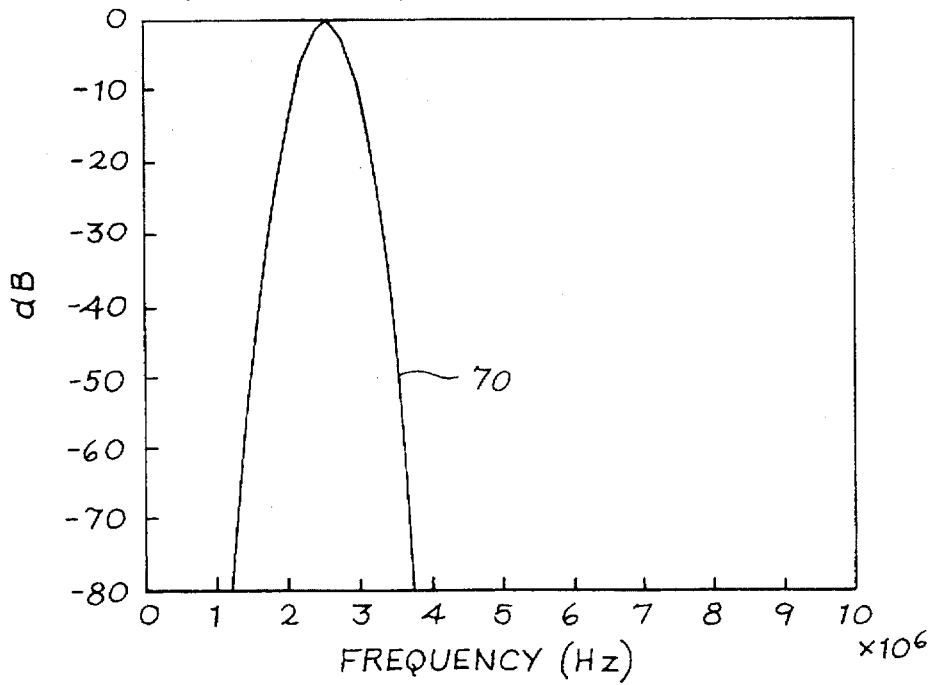
FIG. 3 is a graph of a Gaussian pulse in the frequency domain.

The waveform stored in the waveform memory 44 is shaped to suppress ultrasonic energy in a wide pass band centered at the harmonic frequency. For example, the spectrum of the desired pulse can be designed on a computer 64. FIG. 3 shows the frequency spectrum of one suitable pulse 70 which is centered at the fundamental frequency of 2.5 MHz and is generally Gaussian in shape. The particular Gaussian shape shown in FIG. 3 has an amplitude reduced by −71 dB at 3.71 MHz. The bandwidth of the pulse 70 is 30% of the center frequency, measured at points −6.8 dB with respect to the peak amplitude. Such a pulse will be referred to herein as a 30% BW Gaussian pulse. Note that the pulse 70 has substantially no energy at 5 MHz, the first harmonic of the fundamental frequency. This invention is not limited to use with Gaussian pulses, and a wide range of spectra can be used.

Figure 4:
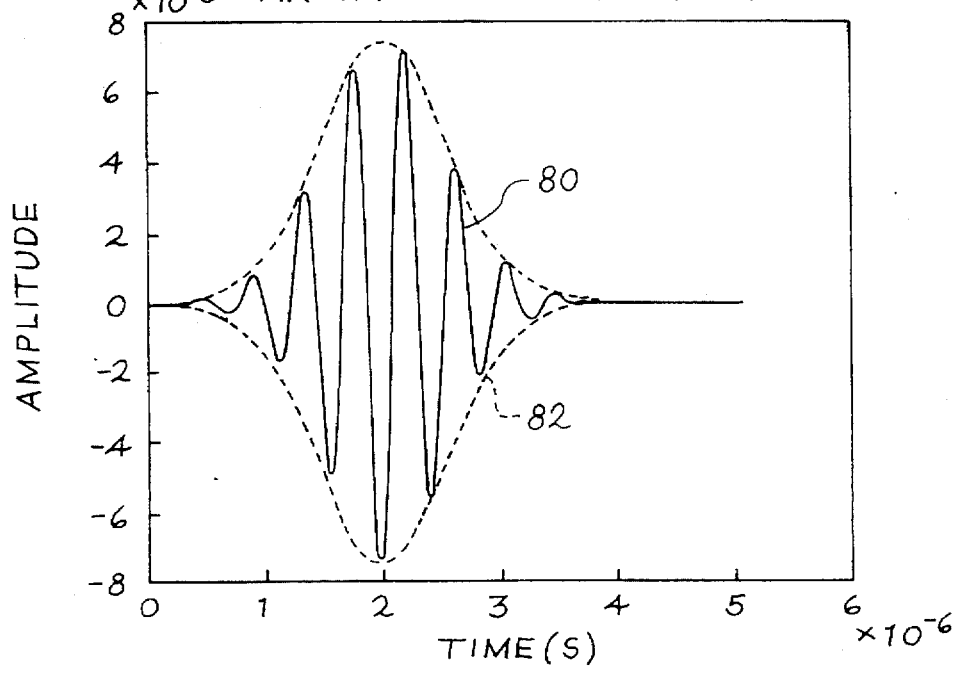
FIG. 4 is a graph of a waveform corresponding to the Gaussian pulse of FIG. 3 in the time domain.

Once the desired pulse has been designed, an inverse fast Fourier transform is then performed to generate the corresponding time domain waveform. FIG. 4 shows a waveform 80 which corresponds to the pulse 70 of FIG. 3. Note that the waveform 80 includes an oscillating component having a frequency of about 2.5 MHz. This oscillating component is shaped by an envelope 82. The envelope 82 rises gradually from zero amplitude to a maximum amplitude, and then falls gradually from the maximum amplitude back to zero amplitude. Thus, the envelope 82 is quite different from the envelope for a switched pulse train, which is substantially rectangular in shape. The gradually increasing and gradually decreasing envelope 82 of FIG. 4 brings with it the advantage of reduced ultrasonic energy at harmonics of the fundamental frequency.

Once a waveform such as the waveform 80 of FIG. 4 has been designed, the waveform 80 can be coded into binary samples at a suitable sample rate and then stored in the waveform memory 44. The waveform memory 44 may be a read only memory, in which case the computer 64 may not be required to be connected to the transmit beamformer 40. Alternately, the waveform memory 44 may be a volatile memory which is programmed at power-up initialization by the computer 64. The computer 64 may perform any desired subset of the pulse designing steps described above. Typically, the desired pulse may be one of several selectable pulses included in a menu for user choice.

When the waveform in the waveform memory 44 is designed as described above, the result is a broad band waveform in the waveform memory 44 which simultaneously has substantially no radiated energy in a broad band centered on the harmonic. In the example of FIGS. 3 and 4, substantially no ultrasonic energy is radiated at frequencies above 4 MHz, or in a bandwidth of ±1 MHz with respect to the first harmonic (5 MHz). Preferably, the energy component at the harmonic is more than −30 dB reduced with respect to the magnitude of the fundamental frequency, and ideally is reduced by more than −40 dB.

Of course, it is not necessary to define the waveform 80 initially in the frequency domain. A Gaussian pulse can be defined in the time domain. Furthermore, the envelope need not be Gaussian, it may be some other window function such as a Hamming pulse, a modified Gaussian pulse, or any other suitable pulse. In some applications it may be preferable to use a narrow bandwidth pulse and thereby achieve a very high reduction of energy at the harmonic, since the harmonic of the lower bandedge is well above the upper bandedge. On other occasions it may be preferable to use a wider bandwidth pulse, for example, to obtain better axial (temporal) resolution. In this case, somewhat reduced reduction of energy at the harmonic may be accepted.

An alternative approach is to design the pulse 70 to ensure that substantially no energy is transmitted above 1.5 times the center frequency of the intended fundamental pulse (3.75 MHz in this case). It is preferable to limit low frequency energy in the transmitted pulse so that the harmonic energy associated with this frequency does not fall within the spectrum of the transmitted pulse. If the cut off frequency is 3.75 MHz, there should be very little transmitted energy below 1.875 MHz.

In designing the pulse 70 and the waveform 80, the Gaussian waveform may be passed through a high order, low pass filter to eliminate all harmonic energy. This filtering may be done off line in the computer 64.

Optimum imaging of the nonlinear contrast agent is obtained when the transmit beam insonifies the agent at power levels within a desired range. Power levels below this range may not be sufficiently high to cause the nonlinear contrast agent to radiate at the harmonic frequency. Power levels above this range may destroy the contrast agent prematurely. Additionally, since there are FDA limits on ultrasound intensity, a sharply focused transmit beam is not optimal. Such a sharply focused beam provides a high intensity (near the FDA limits) at the focus, but an intensity that is indesirably low at many other points along the associated receive scan line.

The receive beamformer 22 preferably receives samples along an entire scan line for each transmit event. For this reason, it is preferable that the region of insonification within the desired power level range be extended over a substantial portion of the length of the receive scan line. Thus, it is preferable that the intensity of the transmitted ultrasonic energy be substantially uniform and at a high level throughout the field of interest (which is typically a large fraction of the displayed depth).

The delay memory 42 preferably stores delay values to provide a controlled spread to the beam intensity in a way to optimize imaging of the contrast agent. Also, by making the intensity of harmonic energy received at the receive beamformer 22 more uniform throughout the field of interest, the levels of harmonic back scatter may be better controlled, resulting in manageable voltage swings at the receiver input.

Figure 5:
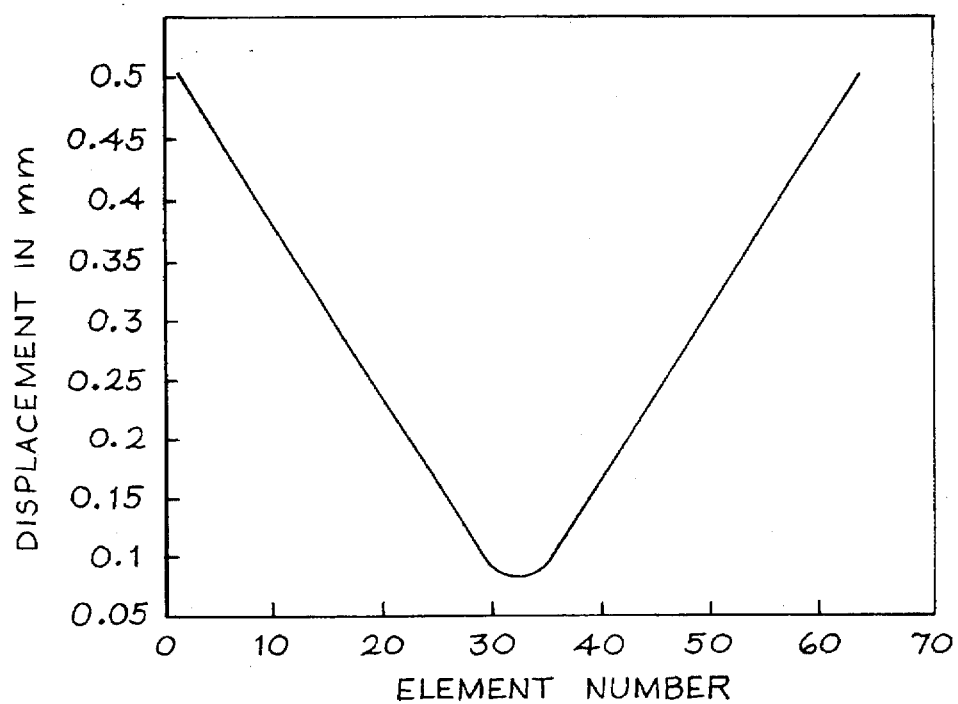
FIG. 5 is a graph of a focusing profile suitable for an axicon focus.

In this embodiment, the delay values stored in the delay memory 42 are selectively chosen to spread the beam along the current ultrasound line. One way to accomplish this is to use the well-known axicon focusing arrangement, as described, for example by C. Burckhardt in "Ultrasound Axicon: A Device for Focusing over a Large Depth" (J. Acoust. Soc. of Am., 54, 6, pp. 1628–1630 (1973)). The axicon focusing arrangement may utilize a focusing profile as shown in FIG. 5. Typically, this focusing profile provides a near focal limit corresponding to a circular arc centered on the near focal limit. Typically, the delay profile extends linearly outwardly from this circular arc to some outer limit, as shown in FIG. 5.

The objective is to spread the ultrasound energy throughout a region of the target, and many different delay profiles may accomplish this result. For example, the delay profile may be slightly curved, with a nonlinear variation of focal point with respect to transducer element position. There may be an outer focal limit, in which case the delay profile can include a circular portion at the ends of the array.

Figure 6:
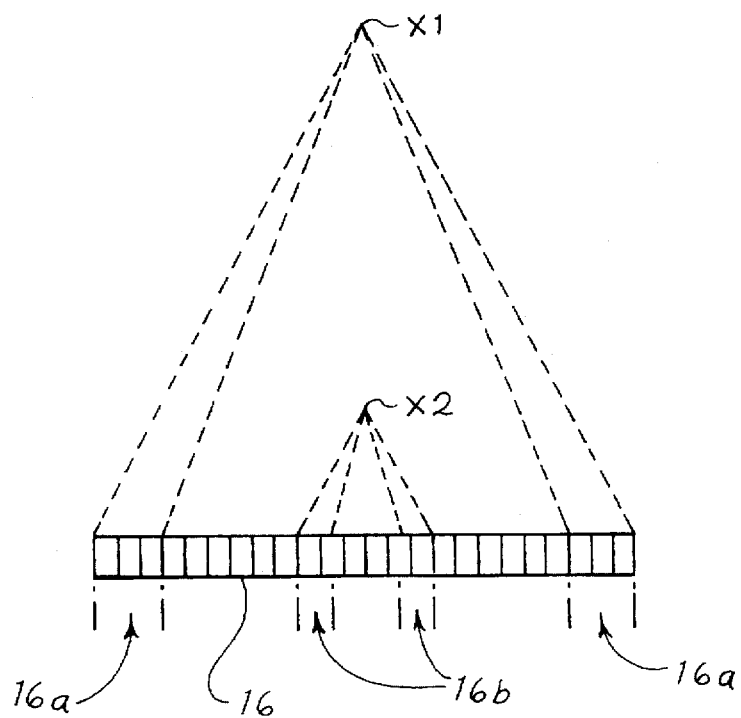
FIG. 6 is a schematic representation of a compound focus arrangement.

In many applications, it will be desirable to select the delay values in the delay memory 42 such that at least first frequency components of the transmit beam from at least a first plurality of transducers are focused at a first, shorter range, and that at least second frequency components of the transmit beam from at least a second plurality of transducers are focused at a second, longer range. One example is shown in FIG. 6, where substantially all of the ultrasonic energy from the transducers 16a at the end portions of the transducer array 16 are focused at a single longer range X1, and substantially all of the ultrasonic energy from the transducers 16b at central portions of the array are focused at a single, shorter range X2. By properly selecting the delay values, a line focus or a multiple-point compound focus may be obtained. When a line focus is used, the line may be straight or curved.

Another approach begins with focal delays required for a chosen focal point in the conventional manner. A random delay error is superimposed on these focal delays to smear or defocus the resulting beam. The greater the degree of defocusing, the more spread out the beam is. Preferably, a user control is provided to allow the user to vary the degree of defocusing by increasing the relative level of the defocusing delays. Also, it is preferable to increase the transmitted energy level to partially compensate for the loss of peak field intensity due to defocusing, either in an automatic (internally programmed) manner or under user control. The defocusing hardware can consist of a modified version of aberration correction hardware in which the delay corrections are pre-programmed random numbers rather than values which are continuously updated, for example by means of cross-correlating the waveforms from adjacent elements.

Conventional imaging at the fundamental frequency using an axicon or defocused beam is known to produce side lobes. However, such side lobes are not anticipated to create substantial problems in this application, particularly if the side lobes are below the harmonic activation threshold intensity and they therefore do not contribute to the generation of harmonic energy. Full dynamic receive focusing is preferably performed in the receive beamformer 22 to reduce the effect of side lobes in the transmit beam further.

Regardless of the precise configuration of the pulse 70 and the waveform 80, the waveform 80 preferably provides more uniform field intensity through a usefully extended depth of field. This results in more uniform generation of harmonic energy by the contrast agent and possibly a higher overall signal to noise ratio since more of the field is being unisonified at a sufficiently high power level to cause the contrast agent to radiate harmonic energy, but at a sufficiently low power level to prevent unnecessarily rapid destruction of the contrast agent.

If desired, the axicon focus may be obtained with a lens. Also, an axicon focusing scheme may be used in the elevation direction, if it is desired to increase the dimension of the insonified region in that direction.

Figure 7:
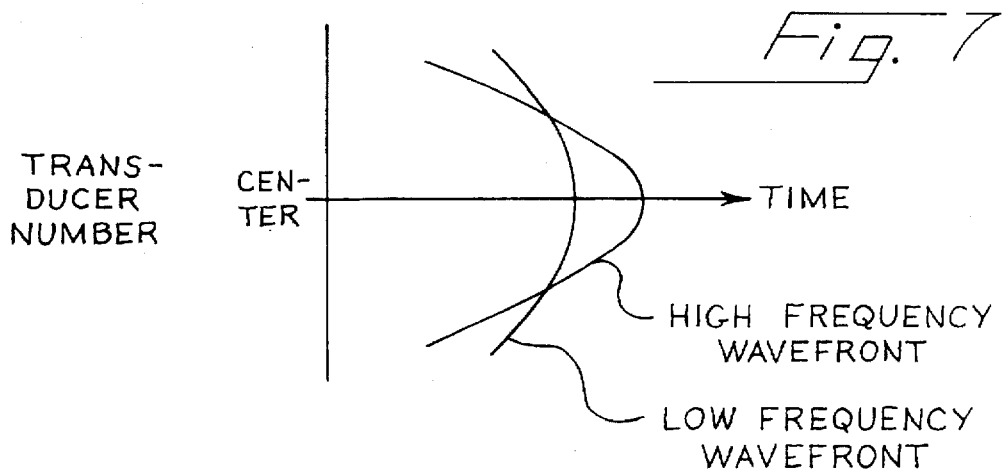
FIG. 7 is a graph showing high and low frequency wavefronts.

The transmit beamformer 40 of FIG. 2 is quite similar to the beamformer shown in FIG. 13 of U.S. patent application Ser. No. 08/397,833, and the techniques described above relating to Gaussian waveforms modified to provide a line focus can be performed in the manner described in the above-identified application. Note in particular pages 23 and 24 of the above-identified application as filed, which expressly relate to optimized transmit beamformers for use with nonlinear contrast agents. With this approach, a plurality of transmit waveforms are provided, each for a respective one of the transducers of the transducer array. This plurality of transmit waveforms includes a central transmit waveform associated with a central one of the transducers. As explained in the above-identified patent application in detail, the central transmit waveform preferably comprises a lower frequency component and a higher frequency component, and a lower frequency component of the central transmit waveform occurs earlier in time than the higher frequency component of the central transmit waveform, as shown in FIG. 7. FIG. 7 corresponds to FIG. 11 of above-identified application Ser. No. 08/397,833, and that application can be referenced for additional information regarding these figures. When the system of application Ser. No. 08/397,833 is adapted for use with this invention, it is preferred that the frequencies along the line focus all be near the fundamental frequency to insonify the non-linear contrast agent effectively.

Additionally, the transmit beamformer described in Cole, et al., U.S. patent application Ser. No. 08/286,652, filed Aug. 5, 1994, and in U.S. patent application Ser. No. 08/432,056, filed May 2, 1995, both assigned to the assignee of the present invention, can be adapted for use with this invention. Once the desired output is defined as described above in terms of very low harmonic signal, one can then define the ideal output signal in the frequency domain and then convert it to the time domain. This time domain signal can then be divided by the carrier to obtain the desired envelope using complex shapes for both the time domain signal and the carrier. This combination of envelope and carrier can then be programmed into the transmit waveformer, using the parameters of attached Appendix 1. Appendix 1 provides parameters for both B-mode and Flow Mode.

The envelope is sampled at a relatively low frequency, and as a result of imperfections in real implementations, remnants of harmonics relating to the sampling frequency of the carrier and the base band signal may appear in the final result.

In this example, harmonic energy at the second harmonic from the contrast agent is imaged using the receive beamformer described in Wright, et al. U.S. patent application Ser. No. 08/286,658, filed Aug. 5, 1994, and in U.S. patent application Ser. No. 08/432,615, filed May 2, 1995, both assigned to the assignee of the present invention. This receive beamformer can be programmed using the parameters of attached Appendix 2.

For example, the transmit beamformer of U.S. patent applications Ser. Nos. 08/286,652 and 08/432,056 can be operated with a nominal center frequency FO equal to 5.0 MHz, a transmit carrier frequency $F_c$ equal to 2.5 MHz, and a Gaussian envelope having a 50% bandwidth at −6.8 dB with λ/4 envelope sampling.

Figure 8:
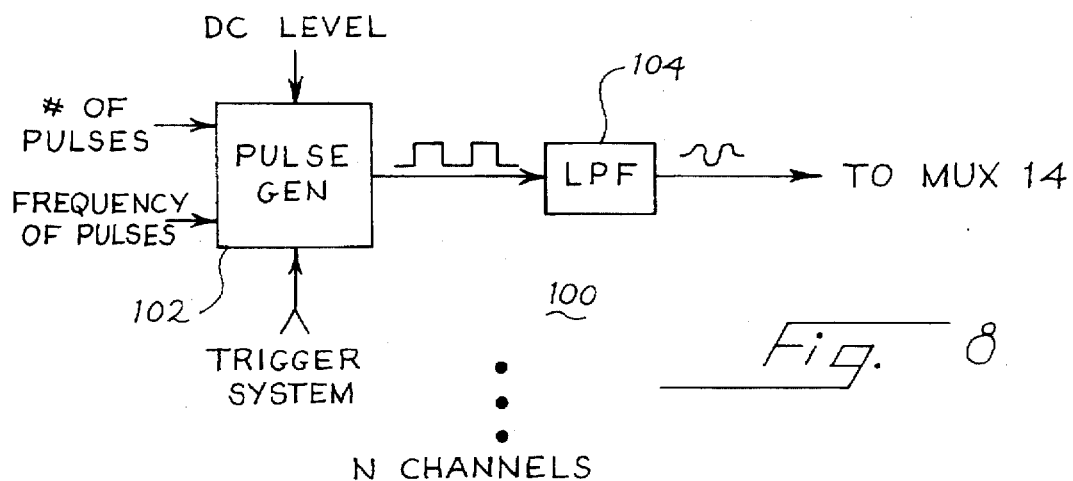
FIG. 8 is a block diagram of a second transmit beamformer suitable for use in the system of FIG. 1.

FIG. 8 shows another transmit beamformer 100 that can be used in the ultrasound imaging system 10. The beamformer 100 includes a pulse generator 102 which supplies a burst of pulses to a low pass filter 104. In this case, the pulse generator 102 switches between a selectable high voltage DC level and ground. The duration of the pulses and the number of pulses in the burst are controllable, as described, for example, in U.S. Pat. No. 4,550,067 (Maslak, et al.), assigned to the assignee of the present invention. The low pass filter 104 is designed as described above to substantially eliminate energy at the harmonic. The low pass filter 104 can be an analog filter such as a suitable Bessel or Chebyshev filter.

Figure 9:
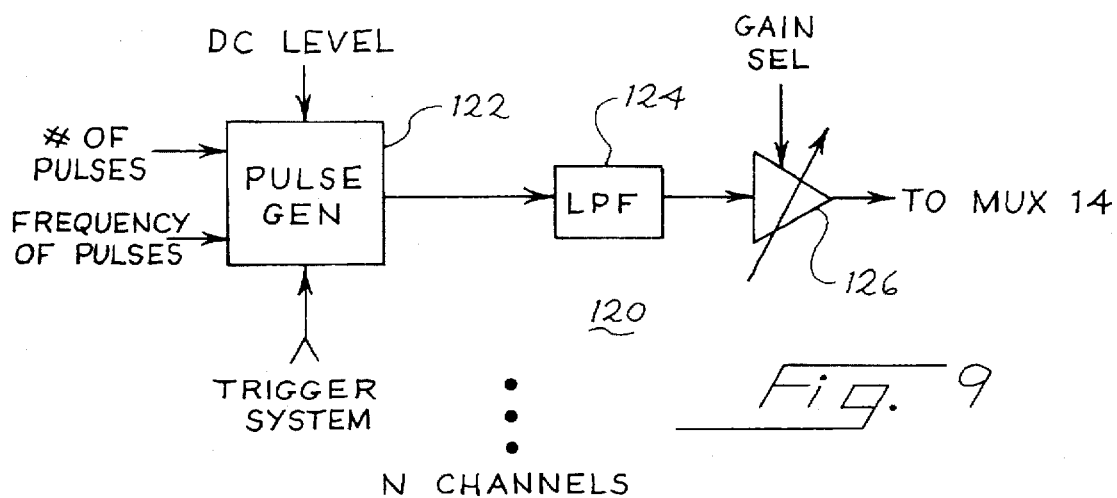
FIG. 9 is a block diagram of a third transmit beamformer suitable for use in the system of FIG. 1.

FIG. 9 shows another transmit beamformer 120 that can be used in the system 10 of FIG. 1. The transmit beamformer 120 includes a pulse generator 122 which supplies pulses to a low pass filter 124. The output of the low pass filter is supplied to a high voltage amplifier 126. Because the low pass filter 124 is applied prior to the amplifier 126, the low pass filter 124 can be designed with smaller components and hence can be higher order and more effective in suppressing harmonic energy.

It should be noted that conventional transducer arrays have a finite bandwidth, such as 75% at the −6 dB levels. Considering the example where the fundamental frequency is 2.5 MHz and the harmonic frequency is 5 MHz, the transducer will typically be centered between the transmit and receive frequencies (as for example at 3.75 MHz), with a relatively high bandwidth. Notice that when this transducer is operated at 2.5 MHz with a symmetrical band shape, the transducer will skew the transmitted spectrum toward higher frequencies. In the design of the transmitted pulse, the spectrum should preferably be modified to take account of the skewing effect of the finite bandwidth effects of the transducer and the fact that the transducer is working away from its center frequency in transmit.

Of course, the techniques described above can be used in systems 10 which provide apodization in the normal manner. If desired, apodization profiles can be modified if experience shows that the contributions from the end transducer elements (which are focused at deep ranges) are too attenuated. In this case, it may be preferable to increase the weighting at the end elements to compensate for this effect to some extent. By operating the end transducer elements at higher power levels than central transducer elements, more nearly uniform power levels are obtained at various ranges in the tissue being imaged.

A further modification is to use fewer transmit lines than receive lines. Since contrast agent tends to be consumed by the insonification process, it is preferable to reduce the number of transmit lines by reducing the frequency of firings and/or the spatial density of lines. Reduced firings and density can be achieved by firing one fourth the number of transmit lines and forming four synthetic receive lines closely spaced around each transmit line, which may be slightly defocused if required. Wright, et al. U.S. patent application Ser. No. 08/418,640, filed Apr. 7, 1995, assigned to the assignee of the present invention, discloses synthetic line systems that can be adapted for this purpose. Furthermore, frames of low intensity ultrasound may be interleaved with high intensity frames.

Multiple transmit zone firing (compound focus) may also yield a better result by spreading the beam between two selected focal regions. These techniques can be implemented on the transmit beamformer described in U.S. patent application Ser. No. 08/286,652, as described above.

From the foregoing, it should be apparent that improved systems and methods for imaging contrast agent have been disclosed. These systems can use the transmit beamformers described in co-pending U.S. patent application Ser. No. 08/397,833, which focuses different frequency components at different ranges. Also, as described above, these techniques can be used with other beamformers which utilize other transmit waveforms. Of course, the various aspects of this invention relating to harmonic suppression and line focus (or other spreading of the region of maximum intensity) can be used separately from one another, rather than in combination as described above. It is intended that the foregoing detailed description be regarded as illustrative rather than limiting. It is the following claims, including all equivalents, which are intended to define the scope of this invention.

APPENDIX 1

Parameters for Transmit Beamformer
(all references are to FIG. 3 of U.S. patent application Ser. No. 08/432,056)

| Parameter | Corresponds to | Value |
|---|---|---|
| h2 | FIR filter h2 of T312 | [1 4 6 4 1] |
| h3 | FIR filter h3 of T324 | [1 0 −2 0 1] |
| Ku2 | Upsampler of T326 | 2 |
| Ku1 | Upsampler of T312 | 2 (determined by: Ku1=Nb*4/Ku2) |
| h4 | FIR filter h4 of T326 | [2 3 2] |
| Nb | Number of transmit beams | 1 |
| cw_on | | 0 −> pulsed mode |
| Envelope Type, beam 0 | 'Env len' of FIG. 4 | 0 −> real |
| Ns | | B-mode: 17 |
| | | F-mode: 23 |
| h1 | Envelope in T304 | B-mode: [0.0039, 0.0156, 0.0430, 0.1133, 0.2461, 0.4531, 0.7031, 0.9141, 0.9961, 0.9141, 0.7031, 0.4531, 0.2461, 0.1133, 0.0430, 0.0156, 0.0039] (33% Gaussian, sampled at Fe=10 MS/s) |
| | | F-mode: [0.0039, 0.0078, 0.0195, 0.0430, 0.0898, 0.1719, 0.2930, 0.4531, 0.6406, 0.8203, 0.9492, 0.9961, 0.9492, 0.8203, 0.6406 0.4531, 0.2930, 0.1719, 0.0898, 0.0430 0.0195, 0.0078, 0.0039] (25% Gaussian, sampled at Fe=10 MS/s) |
| phi | Phase to be applied at T310 | See definition of phi below |
| Fs | Sampling Freq at O/P of T328 | 40 MS/s |
| Fe | Sampling Freq of envelope in T304 | 10 MS/s (determined from above based on: Fe=Fs/Ku1/Ku2 |
| Fpa select | v_phi=Fc/F0 | 0 −> use modulation frequency for focusing |
| Fm/F0 | v=Fc/F0 | 0.5 (Fm=2.5 MHz; F0=5.0 MHz) |
| F0 | | 5.0 MHz |

Together these terms, plus the fact that the envelope is real, are used to calculate the phase applied in complex multiplier T310, as described in Application Ser. No. 08/432,056. In particular, this phase is broken into:

| | |
|---|---|
| envelope phase | zero because envelope is real |
| fine focusing | calculated from the difference between quantized and ideal delay, using the phase alignment frequency vphi=v |
| modulation | complex multiplier T310 includes a component which corresponds to modulation to a frequency (Fm/F0−1)*F0. This modulation, in combination with later modulation in complex multiplier T318, results in an overall effective modulation frequency Fm. |

$phi = phi\_D + phi\_E + phi\_R$ phi_D   (Phase portion of-delay (fine focusing)) = $-2.(pi).v\_phi.tau\_phi$
   tau_phi = low order portion of the delay word representing fractional units of T0 (1/F0) as in Pat Appl 08/432,056.
   This is the portion of the specified focusing delay which is applied via phasing rather than true time delay phi_E =   0 (Waveform sample phase is zero because envelope is real)

phi_R =   $2.(pi).ku1.(v - 1).n/4$ (n is the successive sample number)
   This ia a phase rotation of $2.(pi).(Fm - F0).t$ where $t = ku1.t / (4.F0)$

APPENDIX 2

Parameters for Receive Beamformer
(all references are to FIG. 3 of U.S. patent application Ser. No. 08/432,615)

| Parameter | Corresponds to | Value |
|---|---|---|
| Fs | Sampling rate Fs at ADC | 40 MS/s |
| Nb | Number of receive beams | 2 |
| Kd1 | Downsampler of R162 | 2 |
| h1 | FIR filter h1 of R160 | [2 3 2] (selected based on Kd1) |
| h1 bypass | | disabled |
| h2 | FIR filter h2 of R164 | [1 0 −1] |
| h2 bypass | | disabled |
| h3 | FIR filter h3 of R167 | [1 4j −8 −10j 8 4j −1] |
| h3 bypass | | disabled |
| Kd2 | Downsampler of R169 | 4 (determined by: Kd2=Nb*4/Kd1) |
| Fb | | 5 MS/s (determined from above, based on Fb=Fs/Kd1/Kd2) |
| Fp select | | 0 −> Fp = Fstart |
| Fd select | | 1 −> Fd = Fstart − Fdownslope*R |
| Fstart/F0 | Fstart | B-mode: Fstart/F0=1.1172 (5.5859 MHz) |
| | | F-mode: Fstart/F0=1.0781 (5.3906 MHz) |
| Fdownslope | {DELTA F sub downshift} | B-mode: Fdownslope = 1.793E-4 F0/T0 <---> 5821 Hz/mm |
| | | F-mode: Fdownslope = 1.144E-4 F0/T0 <---> 3716 Hz/mm |

APPENDIX 2-continued

Parameters for Receive Beamformer
(all references are to FIG. 3 of U.S. patent application Ser. No. 08/432,615)

| Parameter | Corresponds to | Value |
|---|---|---|
| Tbreak | | Tbreak >= 1792 TO (276 mm) |
| Fupslope | | 0 |
| Base Band Filter | | |
| Ntaps | | 16 |
| type | | real |
| L/M ratio | | 1/1 (based on L=1, M=1) |
| hbbf | Base band filter coefficients | (based on L=1, M=1)<br>B-mode: hbbf= [0, 0, 0, 0, 0,<br>0.0195, 0.0996, 0.2285, 0.2988, 0.2285,<br>0.0996, 0.0195, 0, 0, 0, 0]<br>F-mode: hbbf= [0, 0, 0, 0.0020, 0.0137,<br>0.0469, 0.1172, 0.1992, 0.2383, 0.1992,<br>0.1172, 0.0469, 0.0137, 0.0020, 0, 0]<br>Baseband filter is an FIR operating on the output of the receive beamformer |

We claim:

1. In a method for imaging a target, said method comprising the steps of (a) transmitting ultrasonic energy at a fundamental frequency and (b) receiving reflected ultrasonic energy at a harmonic of the fundamental frequency, the improvement wherein step (a) comprises the step of:

(a1) transmitting ultrasonic energy in power bursts, each power burst comprising a respective envelope shape, each envelope shape rising gradually to a respective maximum value and falling gradually from the respective maximum value.

2. The method of claim 1 wherein said power bursts are characterized by a power level at the harmonic which is reduced by at least −30 dB with respect to ultrasonic power in the power burst at the fundamental frequency.

3. In a method for imaging a target, said method comprising the steps of (a) transmitting ultrasonic energy at a fundamental frequency and (b) receiving reflected ultrasonic energy at a harmonic of the fundamental frequency, the improvement wherein step (a) comprises the steps of:

(a1) generating a transmit waveform; and (a2) filtering the transmit waveform with a filter adapted to reduce ultrasonic energy in the transmit waveform at the harmonic of the fundamental frequency to at least −30 dB with respect to the fundamental frequency.

4. The method of claim 3 wherein step (a) further comprises the step of:

(a3) amplifying the transmit waveform in a voltage amplifier, wherein step (a3) is performed before step (a2).

5. The method of claim 3 wherein step (a) further comprises the step of:

(a3) amplifying the transmit waveform in a voltage amplifier, wherein step (a3) is performed after step (a2).

6. The method of claim 3 wherein step (a1) comprises the step of using a pulse generator to generate the transmit waveform.

7. The method of claim 3 wherein the filter is adapted to reduce ultrasonic energy in the transmit waveform at the harmonic of the fundamental frequency to at least −40 dB with respect to the fundamental frequency.

8. The method for imaging a target, said method comprising the steps of (a) transmitting ultrasonic energy at a fundamental frequency and (b) receiving reflected ultrasonic energy at a harmonic of the fundamental frequency, the improvement wherein step (a) comprises the step of:

(a1) generating a transmit waveform with a programmable waveform generator such that ultrasonic power in the transmit waveform at the harmonic of the fundamental frequency is reduced by at least −30 dB with respect to ultrasonic power in the transmit waveform at the fundamental frequency.

9. The method of claim 8 wherein ultrasonic power in the transmit waveform at the harmonic of the fundamental frequency is reduced by at least −40 dB with respect to ultrasonic power in the transit waveform at the fundamental frequency.

10. In a method for imaging a target, said method comprising the steps of (a) transmitting ultrasonic energy at a fundamental frequency and (b) receiving reflected ultrasonic energy at a harmonic of the fundamental frequency, the improvement wherein step (a) comprises the step of:

(a1) focusing ultrasonic energy in a transmit beam having a line focus.

11. The method of claim 10 wherein step (a1) comprises the step of phasing a plurality of transmit waveforms to form the line focus for the transmit beam.

12. The method of claim 11 wherein the plurality of transmit waveforms comprises a central transmit waveform associated with a central one of the transducers, wherein the central transmit waveform comprises a lower frequency component and a higher frequency component, and wherein the lower frequency component of the central transmit waveform occurs earlier in time than the higher frequency component of the central transmit waveform.

13. In a method for imaging a target, said method comprising the steps of (a) transmitting ultrasonic energy at a fundamental frequency and (b) receiving reflected ultrasonic energy at a harmonic of the fundamental frequency, the improvement wherein step (a) comprises the step of:

(a1) focusing ultrasonic energy in a transmit beam having an elongated high power region by focusing at least first selected frequency components from at least a first plurality of transducer elements at a first range and focusing at least second frequency components from at least a second plurality of transducer elements at a second range.

14. The method of claim 13 wherein step (a1) comprises the step of phasing a plurality of transmit waveforms to form the transmit beam having the elongated high power region.

15. The method of claim 13 wherein the first range is greater than the second range, and wherein the first plurality of transducer elements are operated at a higher power level than the second plurality of transducer elements.

16. The method of claim 13 wherein step (a1) comprises the step of varying apodization of the first and second transducer elements to achieve more nearly uniform ultrasonic energy levels at the first and second ranges.

17. The method of claims 1 or 3 or 8 or 10 or 13 wherein the tissue comprises a non-linear contrast agent during step (a).

18. In a method for imaging a target, said method comprising the steps of (a) transmitting ultrasonic energy at a fundamental frequency and (b) receiving reflected ultrasonic energy at a harmonic of the fundamental frequency, the improvement wherein step (a) comprises the step of:

(a1) transmitting ultrasonic energy in power bursts, each power burst characterized by a respective frequency spectrum having a respective center frequency, a respective peak amplitude, and a respective bandwidth, the bandwidth of each power burst being at least about 30% of the respective center frequency at points −6.8 dB with respect to the respective peak amplitude, said frequency spectra reduced at the harmonic by more than −30 dB with respect to the peak amplitude.

19. The method of claim 18 wherein the bandwidth of each power burst is at least about 50% of the respective center frequency at points −6.8 dB with respect to the respective peak amplitude.

20. The method of claim 18 or 19 wherein the frequency spectra are reduced at the harmonic by at least about −50 dB with respect to the peak amplitude.

21. The method of claim 18 wherein the power bursts are bipolar.

22. The method of claim 18 wherein the power bursts are unipolar.

23. In a method for imaging a target, said method comprising the steps of (a) transmitting ultrasonic energy at a fundamental frequency and (b) receiving reflected ultrasonic energy at a harmonic of the fundamental frequency, the improvement wherein step (a) comprises the step of:

(a1) transmitting ultrasonic energy in power bursts, each power burst characterized by a respective frequency spectrum having a respective peak amplitude near the fundamental frequency, said frequency spectrum reduced within a first bandwidth greater than or equal to ±X% of the harmonic of the fundamental frequency by more than −YdB with respect to the peak amplitude, where X is equal to 5 and Y is equal to 30.

24. The method of claim 23 wherein X is equal to 10.

25. The method of claim 23 wherein X is equal to 15.

26. The method of claim 23 wherein X is equal to 20.

27. The method of claim 23 wherein X is equal to 10 and Y is equal to 50.

28. The method of claim 23 wherein X is equal to 15 and Y is equal to 50.

29. The method of claim 23 wherein X is equal to 20 and Y is equal to 50.

30. The method of claim 23, 24, 25, 26, 27, 28 or 29 wherein each frequency spectrum has a respective center frequency, a respective peak amplitude, and a respective second bandwidth, the second bandwidth of each frequency spectrum being at least about 30% of the respective center frequency at points −6.8 dB with respect to the respective peak amplitude.

31. The method of claim 30 wherein the second bandwidth of each frequency spectrum is at least about 50% of the respective center frequency at points −6.8 dB with respect to the respective peak amplitude.

32. The method of claim 30 wherein each frequency spectrum is reduced at the harmonic by at least −50 dB with respect to the respective peak amplitude.

33. In an ultrasonic imaging system comprising a transmit beamformer operative to transmit energy at a fundamental frequency, and a receive beamformer responsive to ultrasonic energy at a harmonic of the fundamental frequency, the improvement comprising:

means, included in the transmit beamformer, for transmitting ultrasonic energy in power bursts, each power burst comprising a respective envelope shape, each envelope shape rising gradually to a respective maximum value and falling gradually from the respective maximum value.

34. The method of claim 33 wherein said power bursts are characterized by a power level at the harmonic which is reduced by at least −30 dB with respect to ultrasonic power in the power burst at the fundamental frequency.

35. In an ultrasonic imaging system comprising a transmit beamformer operative to transmit energy at a fundamental frequency, and a receive beamformer responsive to ultrasonic energy at a harmonic of the fundamental frequency, the improvement comprising:

means, included in the transmit beamformer, for generating a transmit waveform; and a filter, responsive to the transmit waveform, to reduce ultrasonic energy in the transmit waveform at the harmonic of the fundamental frequency by at least −30 dB with respect to the fundamental frequency.

36. The invention of claim 35 wherein the filter is adapted to reduce ultrasonic energy in the transmit waveform at the harmonic of the fundamental frequency by at least −40 dB with respect to the fundamental frequency.

37. In an ultrasonic imaging system comprising a transmit beamformer operative to transmit energy at a fundamental frequency, and a receive beamformer responsive to ultrasonic energy at a harmonic of the fundamental frequency, the improvement comprising:

a programmable waveform generator, included in the transmit beamformer, operative to generate a transmit waveform in which ultrasonic power in the transmit waveform at the harmonic of the fundamental frequency is reduced by at least −30 dB with respect to ultrasonic power in the transmit waveform at the fundamental frequency.

38. The invention of claim 37 wherein ultrasonic power in the transmit waveform at the harmonic of the fundamental frequency is reduced by at least −40 dB with respect to ultrasonic power in the transit waveform at the fundamental frequency.

39. In an ultrasonic imaging system comprising a transmit beamformer operative to transmit energy at a fundamental frequency, and a receive beamformer responsive to ultrasonic energy at a harmonic of the fundamental frequency, the improvement comprising:

means, included in the transmit beamformer, for focusing ultrasonic energy in a transmit beam having a line focus.

40. In an ultrasonic imaging system comprising a transmit beamformer operative to transmit energy at a fundamental frequency, and a receive beamformer responsive to ultrasonic energy at a harmonic of the fundamental frequency, the improvement comprising:

means, included in the transmit beamformer, for focusing ultrasonic energy in a transmit beam having an elongated high power region by focusing at least first selected frequency components from at least a first plurality of transducer elements at a first range and focusing at least second frequency components from at least a second plurality of transducer elements at a second range.

41. The invention of claim 40 wherein the first range is greater than the second range, and wherein the first plurality of transducer elements are operated at a higher power level than the second plurality of transducer elements.

42. In an ultrasonic imaging system comprising a transmit beamformer operative to transmit energy at a fundamental frequency, and a receive beamformer responsive to ultrasonic energy at a harmonic of the fundamental frequency, the improvement comprising:

means, included in the transmit beamformer, for transmitting ultrasonic energy in power bursts, each power burst characterized by a respective frequency spectrum having a respective center frequency, a respective peak amplitude, and a respective bandwidth, the bandwidth of each power burst being at least about 30% of the respective center frequency at points −6.8 dB with respect to the respective peak amplitude, said frequency spectra reduced at the harmonic by more than −30 dB with respect to the peak amplitude.

43. The invention of claim 42 wherein the bandwidth of each power burst is at least about 50% of the respective center frequency at points −6.8 dB with respect to the respective peak amplitude.

44. The invention of claim 42 or 43 the frequency spectra are reduced at the harmonic by at least about −50 dB with respect to the peak amplitude.

45. In an ultrasonic imaging system comprising a transmit beamformer operative to transmit energy at a fundamental frequency, and a receive beamformer responsive to ultrasonic energy at a harmonic of the fundamental frequency, the improvement comprising:

means, included in the transmit beamformer, for transmitting ultrasonic energy in power bursts, each power burst characterized by a respective frequency spectrum having a respective peak amplitude near the fundamental frequency, said frequency spectrum reduced within a first bandwidth greater than or equal to ±X% of the harmonic of the fundamental frequency by more than −YdB with respect to the peak amplitude, where X is equal to 5 and Y is equal to 30.

46. The invention of claim 45 wherein X is equal to 10.
47. The invention of claim 45 wherein X is equal to 15.
48. The invention of claim 45 wherein X is equal to 20.
49. The invention of claim 45 wherein X is equal to 10 and Y is equal to 50.
50. The invention of claim 45 wherein X is equal to 15 and Y is equal to 50.
51. The invention of claim 45 wherein X is equal to 20 and Y is equal to 50.
52. The invention of claim 45, 46, 47, 48, 49, 50, or 51 wherein each frequency spectrum has a respective center frequency, a respective peak amplitude, and a respective second bandwidth, the second bandwidth of each frequency spectrum being at least about 30% of the respective center frequency at points −6.8 dB with respect to the respective peak amplitude.

53. The invention of claim 52 wherein the second bandwidth of each frequency spectrum is at least about 50% of the respective center frequency at points −6.8 dB with respect to the respective peak amplitude.

54. The invention of claim 52 wherein each frequency spectrum is reduced at the harmonic by at least −50 dB with respect to the respective peak amplitude.

* * * * *

UNITED STATES PATENT AND TRADEMARK OFFICE
CERTIFICATE OF CORRECTION

PATENT NO. : 5,740,128
DATED : April 14, 1998
INVENTOR(S) : John A. Hossack et al.

It is certified that error appears in the above-indentified patent and that said Letters Patent is hereby corrected as shown below:

Title page,
<u>Page 2</u>

In column 1, line 4, replace "Ultrasoncis" with --Ultrasonics--.

<u>In the Claims</u>

In claim 30, line 1, replace "claim" with --claims--.

In claim 52, line 1, replace "claim" with --claims--.

Signed and Sealed this

Thirty-first Day of August, 1999

Attest:

Q. TODD DICKINSON

*Attesting Officer*    *Acting Commissioner of Patents and Trademarks*